(12) United States Patent
Drent et al.

(10) Patent No.: US 7,265,242 B2
(45) Date of Patent: *Sep. 4, 2007

(54) PROCESS FOR THE CARBONYLATION OF ETHYLENICALLY OR ACETYLENICALLY UNSATURATED COMPOUNDS

(75) Inventors: Eit Drent, Amsterdam (NL); Willem Wabe Jager, Amsterdam (NL); Robert Ian Pugh, Nottingham (GB)

(73) Assignee: Shell Oil Company, Houston, TX (US)

( * ) Notice: Subject to any disclaimer, the term of this patent is extended or adjusted under 35 U.S.C. 154(b) by 374 days.

This patent is subject to a terminal disclaimer.

(21) Appl. No.: 10/996,989

(22) Filed: Nov. 24, 2004

(65) Prior Publication Data

US 2005/0192457 A1    Sep. 1, 2005

(51) Int. Cl.
C07C 67/36 (2006.01)
C07C 51/10 (2006.01)
B01J 31/00 (2006.01)

(52) U.S. Cl. .................. 560/232; 562/517; 502/162; 502/233

(58) Field of Classification Search .......... 560/232; 562/517; 502/162
See application file for complete search history.

(56) References Cited

U.S. PATENT DOCUMENTS

| 5,495,041 | A | 2/1996 | Sielcken et al. ............ 560/207 |
| 6,639,091 | B2 * | 10/2003 | Drent et al. ................... 556/21 |
| 6,706,912 | B2 * | 3/2004 | Drent et al. ................ 560/233 |
| 7,135,542 | B2 * | 11/2006 | Drent et al. ................ 528/310 |
| 7,202,193 | B2 * | 4/2007 | Drent et al. ................ 502/213 |
| 2003/0073868 | A1 | 4/2003 | Hoge, II et al. ............. 568/10 |
| 2006/0235241 | A1 | 10/2006 | Drent et al. ................ 560/207 |

FOREIGN PATENT DOCUMENTS

| DE | 10148712 | 4/2003 |
| EP | 81149 | 6/1983 |
| EP | 273489 | 7/1988 |
| EP | 495548 | 7/1992 |
| EP | 565199 | 10/1993 |
| EP | 1121367 | 5/2003 |
| WO | 96/19434 | 6/1996 |
| WO | 98/42717 | 10/1998 |
| WO | 00/21970 | 4/2000 |
| WO | 01/68583 | 9/2001 |
| WO | 01/72697 | 10/2001 |
| WO | 02/64249 | 8/2002 |

OTHER PUBLICATIONS

"Steric Effects of Phosphorus Ligands in Organometallic Chemistry and Homogeneous Catalysis", Chemical Review,1977, vol. 77, pp. 313-348.
"4-Phosphorinanones II", Journal of Organic Chemistry, J.Am. Chem. Soc., 27 (1962) 1824-1827.
Glegg W et al: "Characterization and Dynamics of [Pd(L-L) H(solv) ]$^+$, [Pd(L-L) (CH$_2$CH$_3$ ) ]$^+$, and [Pd(L-L) (C(O)Et) (THF) ]$^+$ (L-L= 1,2-(CH$_2$PBu$^t_2$)$_2$C$_6$H$_4$) : Key Intermediates in the Catalytic Methooxycarbonylation of Ethene to Methylpropanoate" Organometallics, ACS, Columbus, OH, US, vol. 21, No. 9.29 Apr. 2002, pp. 1832-1840.

* cited by examiner

Primary Examiner—Sikarl A. Witherspoon

(57) ABSTRACT

A process for the carbonylation of unsaturated compounds by contacting the unsaturated compound with carbon monoxide in the presence of a catalyst system comprising:
(a) a source of palladium and/or platinum; and
(b) an unsymmetrical bidentate diphosphine ligand of formula I,

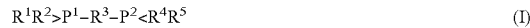

$$R^1R^2{>}P^1{-}R^3{-}P^2{<}R^4R^5 \qquad (I)$$

wherein $P^1$ and $P^2$ represent phosphorus atoms; $R^3$ represents a divalent organic bridging group; and $R^1$, $R^2$, $R^4$ and $R^5$ each individually, or $R^1$ and $R^2$ jointly, and/or $R^4$ and $R^5$ jointly represent organic groups that are covalently linked to the phosphorus; and wherein $R^1$, $R^2$, $R^4$ and $R^5$ are chosen in such way, that the phosphino group $R^1R^2{>}P^1$ differs from the phosphino group $P^2{<}R^4R^5$.

20 Claims, No Drawings

PROCESS FOR THE CARBONYLATION OF ETHYLENICALLY OR ACETYLENICALLY UNSATURATED COMPOUNDS

CROSSREFERENCE TO PRIOR APPLICATIONS

This application claims priority to European Patent Application No. 04251065.1 filed on Feb. 26, 2004. The application also claims priority to International Application PCT/EP 2004/050820 filed May 17, 2004 which claims priority to European Patent Application No. 03076568.9 filed May 22, 2003, now abandoned.

FIELD OF THE INVENTION

The present invention provides a process for the carbonylation of ethylenically or acetylenically unsaturated compounds.

BACKGROUND OF THE INVENTION

In this specification, the term carbonylation refers to the reaction of alkenes or alkynes, i.e. ethylenically or acetylenically non-conjugated unsaturated compounds, under catalysis by a transition metal complex with carbon monoxide and a co-reactant having a mobile hydrogen atom, as for instance described in EP-A-0,495,548 and EP-A-0,565,199, WO-A-96/19434, WO-A-98/42717, WO-A-01/68583 and WO-A-01/72697. This process results in carboxylic acid products, or carboxylic acid derivatives, such as esters, amides or anhydrides, depending on the nature of the co-reactant.

EP-A-0,495,548 discloses a catalyst system comprising a palladium cation and diphosphine bidentate ligands bearing di-alkyl-substituted phosphino groups, such as for instance 1,3 bis(di-tertiary butyl phosphino)propane, and the use of such catalysts in various carbonylation reactions.

Although the disclosed catalyst systems show a good activity in carbonylation reactions, application of the process on an industrial scale requires further improvements in catalyst activity and selectivity for the desired products.

SUMMARY OF THE INVENTION

It has now been found that catalyst systems based on a metal cation selected from 8, 9 or 10 of the Periodic Table of Elements and an unsymmetrical diphosphine ligand exhibit improved catalyst activity in the carbonylation of ethylenically or acetylenically unsaturated compounds, thereby resulting in a significantly improved carbonylation process.

Accordingly, the subject invention relates to a process for the carbonylation of an ethylenically or acetylenically unsaturated compound by contacting the unsaturated compound with carbon monoxide and a co-reactant having a mobile hydrogen atom in the presence of a catalyst system comprising:

(a) a source of a palladium and/or platinum; and
(b) an unsymmetrical diphosphine of formula I,

(I)

wherein $P^1$ and $P^2$ represent phosphorus atoms; $R^3$ represents a divalent organic bridging group; and $R^1$, $R^2$, $R^4$ and $R^5$ each individually, or $R^1$ and $R^2$ jointly, and/or $R^4$ and $R^5$ jointly represent organic substituents that are covalently bound to the phosphorus atom; with the proviso that $R^1$, $R^2$, $R^4$ and $R^5$ are selected in such way, that the phosphino group $R^1R^2$>$P^1$ is different from the phosphino group $P^2$ <$R^4R^5$.

DETAILED DESCRIPTION OF THE INVENTION

The subject process makes use of a catalyst system obtainable by combining (a) a source of a metal cation of palladium or, platinum with a diphosphine ligand as defined above. A source of one or more these metal cations may be used in the various carbonylation reactions. Of these metal cations, palladium (Pd) is particularly preferred for carbonylation reactions involving olefinically unsaturated substrates, whereas platinum (Pt) is highly preferred for acetylenically unsaturated substrates, and for ethylenically unsaturated compounds if branched products are desired.

Examples of suitable metal sources are metal compounds such as salts of Pd and/or Pt and nitric acid, sulphuric acid or sulphonic acids, salts of Pd and Pt and/or carboxylic acids with up to 12 carbon atoms, Pd and/or Pt complexes, e.g. with carbon monoxide and/or acetyl acetonate, or Pd and/or Pt combined with a solid material such as an ion exchanger. Pd and/or Pt acetate and acetyl acetonate are examples of preferred metal sources.

The catalyst system further comprises as component (b) an unsymmetrical diphosphine of formula I,

(I)

wherein $P^1$ and $P^2$ represent phosphorus atoms, $R^3$ represents a divalent organic bridging group, and $R^1$, $R^2$, $R^4$ and $R^5$ each individually, or $R^1$ and $R^2$ jointly and/or $R^4$ and $R^5$ jointly represent organic substituents that are covalently bound to the phosphorus atom; with the proviso that $R^1$, $R^2$, $R^4$ and $R^5$ are selected in such way, that the phosphino group $R^1R^2$>$P^1$ is different from the phosphino group $P^2$<$R^4R^5$.

The beneficial effect of an unsymmetrical diphosphine compared to the corresponding symmetrical diphosphines is exhibited even if the substituents R1 and R2 attached to P1 are very similar to the substituents R4 and R5 attached to P2. Without wishing to be bound to any particular theory, it is believed that the difference in substituents results in a difference in the electron density at the phosphorus atoms. The presence of two binding phosphorus sites with different electronic density in the ligands then appears to have a beneficial effect on the reaction rate. The difference in electron donating ability of the phosphino fragments $P^1R^1R^2$ and $P^2R^4R^5$ of the subject ligands may conveniently be measured by method developed by C. Tolman for monodentate phosphine ligands as described in Chemical Reviews, 1977, Vol. 77, pages 313-348. In this method, the electron-donating ability of a phosphine ligand is determined by reacting one equivalent of a (monodentate) phosphine with Ni(CO)4 to make $P^1R^1R^2$ a Ni(CO)$_3$(phosphine) complex, and then measuring the carbonyl nCO IR stretching frequency (very sharp at high energy mode) of the Ni(CO)$_3$ (phosphine) complex. The more electron density the phosphine ligand donates to a metal centre, and hence the higher the electron-donating ability, the lower the nCO IR stretching frequency measured. In the diphosphine (b), even if only one of the substituents $R^1$, $R^2$, $R^4$ or $R^5$ differs from the other substituents, the two phosphorus atoms will have a different electron density.

The substituents R1 to R4 are thus selected in such way, that one of the phosphorus atoms P1 or P2 has a lower electron density than the other phosphorus atom, as illustrated by a separate, lower nCO IR stretching frequency that can be measured for a transition metal carbonyl complex of the ligand (b). The difference in electron density between the phosphorus atoms $P^1$ or $P^2$ may conveniently be achieved by selecting at $R^1$, $R^2$, $R^4$ and $R^5$ in such way, that one of the phosphorus atoms $P^1$ or $P^2$ has at least one more electron donating substituent $R^1$ and/or $R^2$, as compared to $R^4$ and $R^5$, or vice versa.

Particularly high catalyst activities were found with ligands wherein $R^1$ and $R^2$ together, or each individually represent electron-donating groups as compared to a $PPh_2$- group, whereas $R^4$ and $R^5$ together or each individually represent an electron-accepting group as compared to a $PPh_2$-group.

Within the context of the subject specification, the term "organic group" represents an unsubstituted or substituted, aliphatic or arylaliphatic radical having from 1 to 30 carbon atoms, which is covalently connected to the phosphorus atom by a carbon atom.

The organic groups $R^1$, $R^2$, $R^4$ and $R^5$ may each independently be a monovalent group, or $R^1$ and $R^2$ together and/or $R^5$ and $R^6$ together may be divalent groups. The groups may further contain one or more heteroatoms such as oxygen, nitrogen, sulfur or phosphorus and/or be substituted by one or more functional groups comprising for example oxygen, nitrogen, sulfur and/or halogen, for example by fluorine, chlorine, bromine, iodine and/or a cyano group.

Although increased catalyst activity as compared to each of the analogous symmetrical ligands was shown by all non-symmetric bidentate ligands tested, a particularly high increase in catalyst activity was found with ligands wherein at least one of $R^1$ and $R^2$, or $R^4$ and $R^5$ represents an organic group containing a tertiary carbon atom through which this group is linked to the phosphorus atom.

A yet higher activity was found where both $R^1$ and $R^2$, or $R^4$ and $R^5$ represent an organic group containing a tertiary carbon atom through which each group is linked to the phosphorus atom, and an even higher and yet unprecedented activity was found where all of $R^1$, $R^2$, $R^4$ and $R^5$ represent an organic group containing a tertiary carbon atom through which each group is linked to the phosphorus atom.

Therefore, most preferably, the subject invention also relates to the process for the carbonylation wherein all of $R^1$, $R^2$, $R^4$ and $R^5$ represent an organic group containing a tertiary carbon atom through which each group is linked to the phosphorus atom.

The tertiary carbon atom through which one or more of the groups $R^1$, $R^2$, $R^4$ or $R^5$ preferably are connected to the phosphorus atom tertiary carbon atom, i.e. a carbon atom covalently bonded to the phosphorus and to three substituents other than hydrogen, may be substituted with aliphatic, cycloaliphatic, or aromatic substituents, or may form part of a substituted saturated or non-saturated aliphatic ring structure, all of which may contain heteroatoms.

Preferably, the tertiary carbon atom of $R^1$ and $R^2$, or $R^4$ and $R^5$ may be substituted with alkyl groups, thereby making the tertiary carbon atom part of a tertiary alkyl group, or by ether groups. Examples of suitable organic groups are tertiary-butyl, 2-(2-methyl)-butyl, 2-(2-ethyl) butyl, 2-(2-phenyl) butyl, 2-(2-methyl) pentyl, 2-(2-ethyl)pentyl, 2-(2-methyl-4-phenyl)-pentyl, and 1-(1-methyl) cyclohexyl groups. Although the groups $R^1$ and $R^2$, or $R^4$ and $R^5$ may be each individually different organic groups, due to the use of lower amounts of different raw materials in the synthesis the groups $R^1$ and $R^2$, or $R^4$ and $R^5$ preferably represent the same tertiary organic group. Yet more preferably, $R^1$ and $R^2$, or $R^4$ and $R^5$ represent tertiary butyl groups. Accordingly, the subject invention also pertains to the process, wherein either both $R^1$ and $R^2$, or both $R^4$ and $R^5$ represent a tertiary butyl group.

The substituents of the second phosphorus atom, i.e. $R^1$ and $R^2$ together, or $R^4$ and $R^5$ together preferably represent a divalent group that is directly attached to the phosphorus atom via two tertiary carbon atoms. This divalent group may have a monocyclic or a polycyclic structure.

Accordingly, $R^1$ and $R^2$ together or $R^4$ and $R^5$ together may also represent an optionally substituted divalent cycloaliphatic group, wherein the cycloaliphatic group is linked to the phosphorus atom via two tertiary carbon atoms. Examples of preferred divalent groups are unsubstituted or substituted C4-C30-alkylene groups in which $CH_2$— groups may be replaced by ether linkages through oxygen atoms, or other hetero groups. Suitable divalent groups include 1,1,4,4-tetramethyl-buta-1,4-diyl-, 1,4-dimethyl-1,4-dimethoxy-buta-1,4-diyl-, 1,1,5,5-tetramethyl-penta-1,5-diyl-, 1,5-dimethyl-1,5-dimethoxy-penta-1,5-diyl-, 3-oxa-1,5-dimethoxy-penta-1,5-diyl-, 3-oxa-1,1,5,5-tetramethyl-penta-1,5-diyl-, 3-oxa-1,5-dimethyl-1,5-dimethoxy-penta-1,5-diyl- and similar divalent radicals. Particularly preferred monocyclic structures comprising $R^1$ and $R^2$ together, or $R^4$ and $R^5$ together include 2,2,6,6-tetrasubstituted phosphinan-4-one or -4-thione structures. Ligands comprising such structures may be conveniently obtained under mild conditions as described in Welcher and Day, Journal of Organic Chemistry, J. Am. Chem. Soc., 27 (1962) 1824-1827, for instance by reaction of a secondary phosphine with 2,6-dimethyl-2,5-heptadien-4-one (also known as diisopropylidene acetone, or phorone).

A particularly preferred polycyclic structure including $R^1$ and $R^2$ or $R^4$ and $R^5$ together is for instance the 2-phospha-tricyclo[3.3.1.{3,7}]decyl group that is substituted in 1,3 and 5 position (thus providing the tertiary carbon atoms through which the group is connected to the phosphorous atom), or a derivative thereof in which one or more of the carbon atoms are replaced by heteroatoms. Tricyclo [3.3.1.1{3,7}]decane is the systematic name for a compound more generally known as adamantane. The 1,3,5-trisubstituted 2-phospha-tricyclo[3.3.1.1{3,7}decyl group or a derivative thereof will thus be referred to as "2-PA" group (as in 2-phosphadamantyl group) throughout the specification. The 2-PA group is substituted on one or more of the 1, 3, 5 positions, and optionally also on the 7 position, with a monovalent organic group $R^7$ from 1 to 20 atoms, preferably from 1 to 10 carbon atoms, yet more preferably from 1 to 6 carbon atoms. Examples of $R^7$ include methyl, ethyl, propyl and phenyl. More preferably, the 2-PA group is substituted on each of the 1, 3, 5 and 7 positions, suitably with identical groups $R^7$, yet more preferably with methyl groups. The 2-PA group further contains preferably additional heteroatoms other than the 2-phosphorus atom in its skeleton. Suitable heteroatoms are oxygen and sulphur atoms. More suitably, these heteroatoms are found in the 6, 9 and 10 positions. The most preferred bivalent radical is the 2-phospha-1,3,5,7-tetramethyl-6,9,10-trioxadamantyl group.

Very good results have been obtained in the carbonylation of ethylenically unsaturated compounds with catalyst system comprising bidentate diphosphine ligands whereby $R^1$ and $R^2$ are each individually organic groups only connected to each other via a phosphorus atom, whereas $R^5$ and $R^6$ together represent a bivalent organic group that is bonded to the second phosphorus atom via two tertiary carbon atoms. Accordingly, especially preferred diphosphine ligands (b) fr the catalyst system according to the subject invention are compounds according to formula (II), wherein $R^1$ together with $R^2$, or $R^4$ together with $R^5$, together with the respective phosphorus atoms $P^1$ or $P^2$, respectively, form a 2-phospha-1,3,5,7-tetramethyl-6,9,10-trioxadamantyl group, or a 2,2,6,6-tetramethyl phosphinan-4-one, and wherein the other substituents R1 and R2, or R4 and R5 each individually represent a tertiary butyl group.

Within the subject application, by a "divalent organic bridging group" $R^3$ is understood the group connecting the phosphorus atoms $P^1$ and $P^2$ via the shortest connection in the ligand. The bridging group $R^3$ preferably may have a structure as represented by formula (III),

wherein $R^a$ and $R^b$ independently represent the same or different optionally substituted methylene groups; $R^b$ represents an organic group comprising the bivalent bridging group $C^1$-$C^2$ through which $R^b$ is connected to $R^a$ and $R^c$; m and n independently represent a natural number in the range of from 0 to 3, wherein the rotation about the bond between the carbon atoms of the bridging group $C^1$ and $C^2$ of the bridging group is restricted at a temperature in the range of from about 0° C. to about 250° C., and wherein the dihedral angle between the plane occupied by the three atom sequence composed of $C^1$, $C^2$ and the atom directly bonded to $C^1$ in the direction of $P^1$, and the plane occupied by the three atom sequence $C^1$, $C^2$ and the atom directly bonded to $C^2$ in the direction of $P^2$, is in the range of from about 0 to about 120°. The terms bond and rotation are as defined in Hendrickson, Cram and Hammond, Organic Chemistry, 3rd Edition, 1970, pages 175 to 201. Rotation according to the subject invention means that the atoms attached to $C^1$ and $C^2$ respectively rotate about the axis that runs through the centre of the bond between $C^1$ and $C^2$. The rotation about a bond is called "free" when the rotational barrier is so low that different conformations are not perceptible as different chemical species on the time scale of the experiment. The inhibition of rotation of groups about a bond due to the presence of a sufficiently large rotational barrier to make the phenomenon observable on the time scale of the experiment is termed "hindered rotation" or "restricted rotation" (as defined in IUPAC Compendium of Chemical Terminology, 2nd Edition (1997), 68, 2209). A suitable experiment can for instance be an $^1$H-NMR-experiment as described in Hendrickson, Cram and Hammond, Organic Chemistry, 3rd Edition, 1970, pages 265 to 281 and in F.A. Bovey, Nuclear Magnetic Resonance Spectroscopy, (New York, Academic Press, 1969), p. 1-20, provided that there are hydrogen atoms present in the ligand that will exhibit a suitable shift influenced by the bond between $C^1$ and $C^2$.

Preferably, there is no free rotation about the bond between $C^1$ and $C^2$ at the temperature range at which the subject process is conducted. This temperature range may conveniently be in between about 0° C. to about 250° C., but preferably the subject process is conducted in the range of from about 10° C. to about 200° C., and yet more preferably in the range of from about 15° C. to about 150° C., and again more preferably in the range of from about 18° C. to about 130° C. The rotation about the bond is considered hindered, if no rotation is measurable in the liquid state or in solution, i.e. at a temperature range where the ligand is liquid if determined under neat conditions, or in solution of a suitable solvent. Accordingly, the rotation about the bond $C^1$-$C^2$ of the bidentate ligand is hindered or restricted in solution or liquid state of the ligand. Preferably, the rotation about the bond $C^1$-$C^2$ of the bidentate ligand is preferably hindered or restricted in the temperature range of the subject process.

The bridging group $R^b$ comprises a chain of 2 optionally substituted carbon atoms $C^1$ and $C^2$. These carbon atoms $C^1$ and $C^2$ form the direct bridge between $R^1R^2P^1$—$R^a{}_m$— and —$R^c{}_n$—$P^2R^5R^6$, so that the phosphorus atoms $P^1$ and $P^2$ and the optionally substituted methylene groups $R^a{}_m$ and $R^c{}_n$ are connected via the bridging group $C^1$-$C^2$ to form the diphosphine ligands (b).

Although many different restricted conformations are possible for the subject ligands, a particular dihedral angle was found to be of high importance for the activity of the catalyst system. A dihedral angle is generally defined as the angle formed by two intersecting planes. The dihedral angle according to the subject process is the angle formed by the plane occupied by the three atom sequence composed of the three atoms $C^2$, $C^1$ and the atom directly bonded to $C^1$ in direction of $P^1$, and the plane occupied by the three atom sequence $C^1$, $C^2$ and the atom directly bonded to $C^2$ in direction of $P^2$ is in the range of from about 0 to about 120°, of the four atom sequence (atom directly bonded to $C^1$ in direction of $P^1$)—$C^1$-$C^2$—(atom directly bonded to $C^2$ in the direction of $P^2$). "In the direction of $P^1$ or $P^2$" herein has the meaning that the relevant atom is situated in that part of the ligand chain that connects $C^1$ and $P^1$, or $C^2$ and $P^2$, respectively.

For instance, in the case that m and n are equal to 1, the dihedral angle is the angle between the plane occupied by the three atom sequence $R^a$—$C^1$-$C^2$ of the four atom sequence $R^a$—$C^1$-$C^2$—$R^c$ and the other three atoms $C^1$-$C^2$—$R^c$ of the four atom sequence $R^a$—$C^1$-$C^2$—$R^c$. Each plane is understood to run through the central points of the respective atoms. In the case that m and n of formula (III) should equal 0, the four atom sequence would accordingly be $P^1$—$C^1$-$C^2$—$P^2$, and the two planes would be defined as $P^1$—$C^1$-$C^2$ and $C^1$-$C^2$—$P^2$.

In the ligands according to the subject process, the dihedral angle as defined above is ranging from 0° to 120°. Since a higher catalytic activity of the catalyst system is thereby obtainable, the dihedral angle preferably is in the range of from about 0° to about 70, yet more preferably in the range of from about 0° to about 15°, and most preferably in the range of from about 0° to about 5°.

Without wishing to be bound to any particular theory, it is believed that ligands allowing rotation about the bond $C^1$-$C^2$ are less able to form a conformationally stable bidentate complex with the palladium centre.

The bond formed between $C^1$ and $C^2$ may be a saturated or an unsaturated bond as occurring in ethylenically unsaturated or aromatic compounds. In the case of a saturated bond connecting $C^1$ and $C^2$, $R^b$ can be expressed by $C^1R'R''$-$C^2R'''R''''$, and the bidentate diphosphine ligand according to the present invention is thus suitably characterised by formula IV

In this embodiment, R' and R", and R''' and R'''' represent hydrogen or the same or different optionally substituted organic group, provided that only one of R' and R", and only one of R''' and R'''' is hydrogen. If $C^1$ and $C^2$ are connected by an ethylenically unsaturated double bond, $C^1$ and C2 also cannot rotate freely. In this case, R can be expressed by $C^1R'$=$C^2R''$, and the bidentate diphosphine ligand according to the present invention is thus suitably characterised by formula (V):

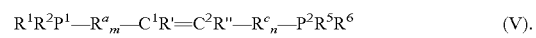

If the bond between $C^1$ and $C^2$ is an ethylenically unsaturated bond, the ligand chain connecting $P^1$ and $P^2$ via $C^1$ and $C^2$ may in principally exist in two isomeric forms, a trans-configuration, and a cis-configuration. According to the above definition, in the trans-configuration the dihedral angle is about 180°, whereas in the cis-configuration, the dihedral angle is about 0°.

The substituents R' to R'''' in formula IV or V can themselves be independent substituents, thus only connected to each other via the carbon atoms $C^1$ and $C^2$, or preferably have at least one further connection. The substituents may further comprise carbon atoms and/or heteroatoms.

The restriction of the free rotation may conveniently be achieved by the bridging group $C^1$-$C^2$ forming part of a molecular structure that impedes rotation about the bond $C^1$-$C^2$ at ambient temperature, and more preferably at a temperature range from about 0 to about 250° C., and preferably from about 15 to about 150° C. This molecular structure may conveniently be for instance a) an ethylenically unsaturated double bond, wherein the rotation is impeded by the energetically advantageous overlap of Π-bonds, and/or b) a cyclic hydrocarbyl structure, in which the rotation is restricted due to the steric interaction of substituents R' to R'''', or due to steric strain induced by a cyclic structure formed by R' to R'''' together, or by combination of the above factors, such as in aromatic or non-aromatic cyclic structures. Conformational stability and hence rigidity may also c) be achieved if the nature of the substituents R' and R'', and/or R''' and R'''' is such that even if not connected to each other they impede rotation about the bond $C^1$-$C^2$, for instance by strong steric interactions. To this goal, yet more preferably, none of R' to R'''' in formula IV or V represent hydrogen.

$R^b$ preferably is a cyclic hydrocarbyl structure that is optionally substituted by hetereoatoms, yet more preferably an aliphatic or aromatic hydrocarbyl structure. This structure may be part of an optionally further substituted saturated or unsaturated polycyclic structure, which also optionally may contain heteroatoms such as nitrogen, sulphur, silicon or oxygen atoms.

Suitable structures $R^b$ include for instance substituted cyclohexyl, cyclohexenyl, cyclohexadienyl, substituted cyclopentane, cyclopentenyl or cyclopentadienyl structures, all of which may optionally contain heteroatoms such as nitrogen, sulphur, silicon or oxygen atoms, with the proviso that the rotation about the bond $C^1$-$C^2$ is restricted, that the dihedral angle is in the range of from about 0° to about 120°, and that there is preferably no rotation about the bond formed by $C^1$ and $C^2$ induced by conformational changes, as for instance in highly restrained acetal structures such as 2,2-dimethyl-1,3-dioxolane. In one particularly preferred embodiment, $R^b$ represents a divalent polycyclic hydrocarbyl ring structure. Such polycyclic groups are particularly preferred due to the high conformational stability and hence high restriction against free rotation about the bond between $C^1$ and $C^2$. Examples of such particularly preferred hydrocarbyl groups include norbornyl, norbornadienyl, isonobornyl, dicylcopentadienyl, octahydro-4,7-methano-1H-indenemethanyl, α- and β-pinyl, and 1,8-cineolyl, all of which may optionally be substituted, or contain heteroatoms as defined above.

In case that the bidentate ligand has chiral centres, it may be in any R,R—, S,S—or R,S—meso form, or mixtures thereof. Both meso forms and racemic mixtures can be employed, provided that the dihedral angle is in the range of from about 0 to about 120°.

In the diphosphine of formula II, $R^b$ preferably represents an optionally substituted divalent aromatic group which is linked to the phosphorus atoms via the groups $R^a$ and $R^c$. Such an aromatic cyclic structure is preferred due to its rigidity, and to a dihedral angle being generally in the range of about 0 to about 5°.

The aromatic group can be a monocyclic group, such as for example a phenyl group or a polycyclic group, such as for example a naphthyl, anthryl or indyl group. Preferably, the aromatic group R contains only carbon atoms, but $R^b$ can also represent an aromatic group wherein a carbon chain is interrupted by one or more hetero atoms, such as nitrogen, sulphur or oxygen atom in for example a pyridine, pyrrole, furan, thiophene, oxazole or thiazole group. Most preferably the aromatic group $R^b$ represents a phenyl group or naphtylene group. Optionally the aromatic group $R^b$ is substituted. Suitable substituents include groups containing hetero-atoms such as halides, sulphur, phosphorus, oxygen and nitrogen. Examples of such groups include chloride, bromide, iodide and groups of the general formula —O—H, —O—X, —CO—X, —CO—O—X, —S—H, —S—X, —CO—S—X, —NH$_2$, —NHX, —NO$_2$, —CN, —CO—NH$_2$, —CO—NHX, —CO—NX$_2$, —CI$_3$ or —CF$_3$, in which X independently represents alkyl groups having from 1 to 4 carbon atoms like methyl, ethyl, propyl, isopropyl and n-butyl. When the aromatic group $R^b$ is substituted it is preferably substituted with one or more aryl, alkyl or cycloalkyl groups, preferably having from 1 to 10 carbon atoms. Suitable groups include methyl, ethyl, trimethyl, iso-propyl, tetramethyl and iso-butyl, phenyl and cyclohexyl.

Most preferably, however, the aromatic group $R^b$ is non-substituted and only linked to the groups $R^a$ and $R^c$ which connect it with the phosphorus atoms. yet more preferably, $R^a$ and $R^c$ are alkylene groups, and thus connected at adjacent positions, for example the 1 and 2 positions, of the aromatic group.

The symbols m and n in formula III, IV and V independently may represent a natural number in the range of from 0 to 3. If the m and n are 0, then the phosphorus atoms $P^1$ and $P^2$ are directly connected to bridge formed by the carbon atoms $C^1$ and $C^2$. If one of m or n equals 0, then either $C^1$ or $C^2$ will be directly connected to $P^1$ or $P^2$. Without wishing to be bound to any particular theory, it is believed that the effect resulting from the particular arrangement of the central bridge formed by $C^1$ and $C^2$ on the phosphorus atoms, and hence on the catalyst complex, will be diluted by the presence of a larger number of groups $R^a$ and/or $R^c$. Also, it is believed that if both m and n equal 0, the distance between the phosphorus atoms may be rather short, such that the ligand binds less strongly to the palladium centre atom of the catalyst complex. Accordingly, due to generally good catalyst activity found with such ligands, m preferably equals 0 or 1, whereas n preferably is in the range of from 1 to 3, more preferably from 1 to 2 and most preferably 1.

If m and/or n have a value above 1, then several optionally substituted groups $R^a$ and $R^c$ connect $P^1$ and $P^2$ to $R^b$. $R^a$ and/or $R^c$. These different may then be the same or individually different groups. Hence, $R^a$ and/or $R^c$ preferably are lower alkylene groups (by lower alkylene groups is understood alkylene groups comprising from 1 to 4 carbon atoms). These alkylene groups can be substituted, for example with alkyl groups or heteroatoms, or non-substituted, and may for instance represent methylene, ethylene, trimethylene, iso-propylene, tetramethylene, iso-butylene and tert-butylene, or may represent methyloxy, ethyloxy and similar groups. Most preferably, at least one of $R^a$ and/or $R^c$ is a methylene group.

Particularly suitable aromatic groups for $R^b$ include aryl groups such as disubstituted phenyl or naphthyl groups, and substituted alkyl phenyl groups such as tolyl and xylyl groups. groups. Preferred due to the high stability of the obtained ligands and catalysts, are tolyl and xylyl groups, wherein the methylene substituent or methylene substituents at the aromatic ring serve as groups $R^a$ and/or $R^c$. Most preferably, $C^1$ and $C^2$ are part of an aromatic ring, whereas at least one of $R^a$ and/or $R^c$ represent methylene groups attached to adjacent atoms $C^1$ and $C^2$ in the aromatic ring.

Accordingly, an especially preferred ligand family according to the subject invention is that wherein $C^1$ and $C^2$ are part of a phenyl ring; m is 0 or 1; n is 1, and $R^a$ and $R^c$ are methylene groups. In yet another especially preferred ligand family due to easy synthetic accessibility, m and n equal 1. Accordingly, such ligands based on the 1,2-di (phosphinomethyl)benzene or 1-phosphino-2-(phosphino methyl)-benzene groups are particularly suited for the subject process due to the high rigidity of the aromatic backbone, easy synthetic availability, and due to the very good results obtained with the derived catalyst system. Such a ligand is for instance 1-(1,3,5,7-tetramethyl-1,3,5-trimethyl-6,9,10-trioxa-2-phosphatricyclo[3.3.1.1$^{\{3,7\}}$]decyl-2-(di-tert-butylphosphinomethyl)benzene.

Very good results were also obtained with unsymmetrical bidentate diphosphine ligand of formula VI,

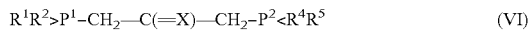

$$R^1R^2 > P^1-CH_2-C(=X)-CH_2-P^2 < R^4R^5 \quad (VI)$$

wherein X represents an oxygen atom, a sulphur atom, an amino group, or a optionally substituted alkylene group, $P^1$ and $P^2$ represent phosphorus atoms; $R^1$, $R^2$, $R^4$ and R5 each individually, or $R^1$ and $R^2$ jointly, and/or $R^4$ and $R^5$ jointly represent organic groups that are covalently linked to the phosphorus; and wherein $R^1$ to $R^4$ are chosen in such way, that the phosphino group $R^1R^2>P^1$ differs from the phosphino group $P^2<R^4R^5$. In these ligands, $R^a$ equals $CH_2$, m is 1, $R^b$ equals $C=CH_2$, and $R^c$ equals $CH_2$. In these ligands, the divalent organic bridging group $R^3$ is represented by the tertiary alkylene carbon atom $C(=X)$. X preferably is an optionally substituted alkylene group, more preferably a methylene group, so that $R^3$ equals $—C(=CH_2)—$. In these ligands, rotation about this carbon atom is also highly restricted due to the stiffness of the alkylene structure, and the dihedral angle formed by $P^1—CH_2—C(=CH_2)—$ and $C(=CH_2)—CH_2—P^2$ is in the range of from about 0° to about 120°.

Preferably, these ligands were employed in a catalyst composition comprising the unsymmetrical bidentate diphosphine ligand and a source of palladium, platinum, or rhodium. The latter was found effective in particular for hydroformulation reaction, i.e. carbonylation reactions ion the presence of a source of hydride, such as molecular hydrogen, in particular in the presence of a source of an anion.

The subject process permits to convert non-conjugated ethylenically and acetylenically unsaturated compounds to the corresponding products with very high turnover numbers due to the high catalyst activity. Suitable ethylenically or acetylenically unsaturated compounds are ethylenically or acetylenically unsaturated compounds having from 2 to 50 carbon atoms per molecule, or mixtures thereof. Suitable ethylenically and acetylenically unsaturated compounds may have one or more isolated unsaturated bonds per molecule. Preferred are compounds having from 2 to 20 carbon atoms, or mixtures thereof, yet more preferred are compounds having at most 18 carbon atoms, yet more at most 16 carbon atoms, again more preferred compounds have at most 10 carbon atoms. The ethylenically or acetylenically unsaturated compound may further comprise functional groups or heteroatoms, such as nitrogen, sulphur or oxide. Examples include carboxylic acids, esters or nitriles as functional groups. In a preferred embodiment, the ethylenically or acetylenically unsaturated compound is an olefin or a mixture of olefins. Such olefins can be converted by reaction with carbon monoxide and a co-reactant with a high regioselectivity towards the linear carbonylation product. Suitable ethylenically or acetylenically unsaturated compounds include acetylene, methyl acetylene, propyl acetylene, ethylene, propylene, butylene, isobutylene, pentene, pentene nitriles, methyl 3-pentenoates, 2- and 3-pentenoic acid. Another preferred feedstock are mixtures of olefins, or mixtures of olefins and saturated compounds obtained for instance in a Fischer-Tropsch synthesis step. In such a synthesis, usually a mixture of olefins and saturated hydrocarbons is obtained. The content of olefins in this mixture may vary, and may be increased by starting of with the synthesis product of an iron-catalyzed Fischer-Tropsch synthesis step. An even higher olefinic content of the mixture may be obtained by catalytic dehydrogenation or thermal cracking in the presence of steam. The subject process in particular suited for reacting such mixtures, as it selectively reacts with olefinic or acetylenically non-conjugated compounds in such a mixture without affecting the other saturated compounds, and hence allows an easy separation of the carbonylated products from the saturated hydrocarbons. According to the subject process, ethylenically or acetylenically unsaturated compounds may be converted into very different chemical compounds, such as aldehydes, esters, acids or acid anhydride, thioesters, amides, and alcohols or others. The specific nature of the product is depending on the nature of the co-reactant having a mobile hydrogen atom. The co-reactant according to the present invention may thus be any compound having a mobile hydrogen atom, and which is capable of reacting as a nucleophile with the diene under catalysis. The nature of the co-reactant largely determines the type of product formed. A suitable co-reactant is water, a carboxylic acid, alcohol, ammonia or an amine, a thiol, or a combination thereof. In other words, the catalyst systems may be used in "hydroformylation reactions", "hydrocarboxylation reactions", "hydroesterification reactions" or "hydroamidation reactions".

Inasmuch as the co-reactant is water, the product obtained will be a carboxylic acid. Anhydrides are obtained inasmuch as the co-reactant is a carboxylic acid. For an alcohol co-reactant, the product of the carbonylation is an ester. Similarly, the use of ammonia ($NH_3$) or a primary or secondary amine $RNH_2$ or R'R"NH will produce an amide, whereas the use of a thiol RSH will produce a thioester. In the above-defined co-reactants, R, R' and/or R" represent optionally heteroatom-substituted organic radicals, preferably alkyl, alkenyl or aryl radicals. When ammonia or amines are employed, a small portion of these co-reactants will react with acids present under formation of an amide and water. Hence, in the case of ammonia or amine-co-reactants, there is always water present. Preferred alcohol co-reactants are alkanols with 1 to 20, more preferably with 1 to 6 carbon atoms per molecule, and alkanediols with 2-20, more preferably 2 to 6 carbon atoms per molecule. The alkanols can be aliphatic, cycloaliphatic or aromatic. Suitable alkanols in the process of the invention include methanol, ethanol, ethanediol, n-propanol, 1,3-propanediol, isopropanol, 1-butanol, 2-butanol (sec-butanol), 2-methyl-1-propanol (isobutanol), 2-methyl-2-propanol (tert-butanol), 1-pentanol, 2-pentanol, 3-pentanol, 2-methyl-1-butanol, 3-methyl-1-butanol (isoamyl alcohol), 2-methyl-2-butanol (tert-amyl alcohol), 1-hexanol, 2-hexanol, 4-methyl-2-pentanol, 3,3-dimethyl-2-butanol, 1-heptanol, 1-octanol, 1-nonanol, 1-decanol, 1,2-ethylene glycol and 1,3-propylene glycol, of which methanol is the most preferred due to the high turn over achievable and due to the particular usefulness of the obtained products. Preferred amines have from 1 to 20, more preferably 1 to 6 carbon atoms per molecule, and diamines have from 2-20, more preferably 2 to 6 carbon atoms per molecule. The amines can be aliphatic, cycloaliphatic or aromatic. More preferred due to the high turnovers achieved are ammonia and primary amines.

Thiol co-reactants can be aliphatic, cycloaliphatic or aromatic. Preferred thiol co-reactants are aliphatic thiols with 1 to 20, more preferably with 1 to 6 carbon atoms per molecule, and aliphatic dithiols with 2-20, more preferably 2 to 6 carbon atoms per molecule.

The subject carbonylation reaction is also known as a hydroformylation reaction in the case that the co-reactant is a hydride source, such as molecular hydrogen. This can be achieved by supplying carbon monoxide and hydrogen to the reaction in equimolar or non-equimolar ratios, e.g. in a ratio within the range of about 5:1 to about 1:5, preferably about 3:1 to about 1:3. Preferably they are supplied in a ratio within the range of about 2:1 to about 1:2, and will result in alcohol mixtures. In particular when Fischer-Tropsch product streams are used as feedstocks, the obtained product mixtures can be suitably used for sanitary or other related applications.

The carbonylation can be suitably carried out at moderate reaction conditions. Hence temperatures in the range of about 50 to about 200° C. are recommended, preferred temperatures being in the range of about 70 to about 160° C. Reaction pressures in the range of about 5 to about 100 bar are preferred, lower or higher pressures may be selected, but are not considered particularly advantageous. Moreover, higher pressures require special equipment provisions.

In the process of the invention, the unsaturated starting material and the formed product as well as the co-reactant may act as reaction solvent. Hence, the use of a separate solvent might not be necessary. Conveniently, however, the carbonylation reaction may be carried out in the additional presence of a solvent, in particular in the start-up phase of the reaction. As such, saturated hydrocarbons, e.g. paraffins and isoalkanes are recommended and furthermore alcohols, the saturated hydrocarbons and alcohols preferably having from 1 to 10 carbon atoms per molecule, such as methanol, butanol, 2-ethylhexan-1-ol, nonan-1-ol, or in general terms the alcohols formed as carbonylation product; ethers such as 2,5,8-trioxanonane (diglyme), diethylether and anisole, and ketones such as methylethylketone. Solvents, comprising or substantially consisting of sulphones are also preferred. Sulphones are in particular preferred, for example dialkyl-sulphones such as dimethyl-sulphone and diethylsulphone and cyclic sulphones, such as sulfolane, 2-methylsulfolane and 2-methyl-4-ethyl-sulfolane.

The ratio of moles of bidentate diphosphine, i.e. catalyst component (b), per mole atom of palladium cations, i.e. catalyst component (a), ranges from about 0.5 to about 10, preferably from about 0.8 to about 8, and yet more preferably from about 1 to about 5. The ratio of moles of bidentate diphosphine, i.e. catalyst component (b), per mole atom of palladium, i.e. catalyst component (a), is not critical. Preferably it ranges from about 0.1 to about 100, more preferably from about 0.5 to about 10.

A more preferred catalyst the active species is based on an equimolar amount of bidentate diphosphine ligand per mole palladium. Thus, the molar amount of bidentate diphosphine ligand per mole palladium is preferably in the range of about 1 to about 3, more preferably in the range of about 1 to about 2, and yet more preferably in the range of about 1 to about 1.5. In the presence of oxygen, slightly higher amounts may be beneficial.

Preferably, the catalyst system or composition further preferably comprises a source of an anion. A suitable source of anion may be a strong, or a weak coordinating anion. Various anions may be used as counter-ion to the metal cation. Examples thereof include anions that are the conjugated base of acids having a pKa (measured at 18° C. in water) of less than 6, preferably less than 4. The anions derived from these acids do not or only weakly co-ordinate with the metal cation, by which is meant that little or no covalent interaction occurs between the anion and the cation. Catalysts based on these anions exhibit a good activity. Suitable anions include anions derived from Bronsted acids, such as from phosphoric acid and sulphuric acid, and in particular from sulphonic acids and (halogenated) carboxylic acids, such as trifluoroacetic acid, 2,6-di chlorobenzoic acid, and 2,6-bis(trifluoromethyl)benzoic acid or trifluoroacetic acid, etc. Anions derived from sulphonic acids are particularly preferred, for example methanesulphonic acid, trifluoromethanesulphonic acid, tert-butanesulphonic acid, p-toluenesulphonic acid and 2,4,6-trimethylbenzenesulphonic acid. Also complex anions are suitable, such as the anions generated by a combination of a Lewis acid such as $BF_3$, $B(C_6F_5)_3$, $AlCl_3$, $SnF_2$, $Sn(CF_3SO_3)_2$, $SnCl_2$ or $GeCl_2$, with a protic acid, preferably having a pKa of less than 5, such as a sulphonic acid, e.g. $CF_3SO_3H$ or $CH_3SO_3H$ or a hydrohalogenic acid such as HF or HCl, or a combination of a Lewis acid with an alcohol. Examples of such complex anions are $BF_2$—, $SnCl_3$—, $[SnCl_2.CF_3SO_3]$— and $PF_6$—. Preferably, the source of anions is a carboxylic acid, which can serve both as promoter component, as well as solvent for the reaction. Again more preferably, the source of anions is an acid having a pKa below 3.6 (measured in aqueous solution at 18° C.), and yet more preferably catalyst component (c) is an acid having a $pK_a$ below about 3.0, and yet more preferably a $pK_a$ of above about 2.0. Examples of suitable acids include acetic acid, propionic acid, butyric acid, pentanoic acid, pentenoic acid and nonanoic acid. Very conveniently the acid corresponding to the desired product of the reaction can be used as the catalyst component (c). Catalyst component (c) can also be an ion exchanging resin containing carboxylic acid groups. This advantageously simplifies the purification of the product mixture.

In the case that the co-reactant is an amine or ammonia, and the source of an anion of the catalyst system is an acid, preferably the amount of ammonia or amine is less than stoichiometric based on the amine functionality. Inadvertently, when the co-reactant is ammonia, and to a lesser extent a primary amine, a small amount of the acid present will react to an amide under liberation of water. Hence, there is also always a small amount of acid formed from the unsaturated compound, carbon monoxide and the water, which in turn replaces acid converted to amide by the direct reaction as described above.

The molar ratio of the source of anions, and palladium, platinum, or rhodium is not critical. However, it suitably is between about 2:1 and about $10^7$:1 and more preferably between about $10^2:1$ and about $10^6:1$, yet more preferably between about $10^2:1$ and about $10^5:1$, and most preferably between about $10^2:1$ and about $10^4:1$ due to the enhanced activity of the catalyst system. Accordingly, if a co-reactant should react with the acid serving as source of anions, then the amount of the acid to co-reactant should be chosen such that a suitable amount of free acid is present. Generally, a large surplus of acid over the co-reactant is preferred due to the enhanced reaction rates.

The quantity in which the complete catalyst system is used is not critical and may vary within wide limits. Usually amounts in the range of about $10^{-8}$ to about $10^{-1}$, preferably in the range of about $10^{-7}$ to about $10^{-2}$ mole atom of palladium per mole of olefin are used, preferably in the range of about $10^{-5}$ to about $10^{-2}$ gram atom per mole. The process may optionally be carried out in the presence of a solvent, however preferably the acid is used as solvent and as promoter.

The carbonylation reaction according to the present invention is carried out at moderate temperatures and pressures. Suitable reaction temperatures are in the range of about 0-250° C., more preferably in the range of about 50-200° C., yet more preferably in the range of from about 80-150° C.

The reaction pressure is usually at least atmospheric. Suitable pressures are in the range of about 0.1 to about 15 MPa (about 1 to about 150 bar), preferably in the range of about 0.5 to about 8.5 MPa (about 5 to about 85 bar). Carbon monoxide partial pressures in the range of about 0.1 to about 8 MPa (about 1 to about 80 bar) are preferred, the upper range of about 4 to about 8 MPa being more preferred. Higher pressures require special equipment provisions.

The carbonylation reaction is further conveniently carried out at a temperature in the range of about 30 to about 200° C., preferred temperatures being in the range of about 50 to about 180° C.

In the process according to the present invention, the carbon monoxide can be used in its pure form or diluted with an inert gas such as nitrogen, carbon dioxide or noble gases such as argon, or co-reactant gases such as ammonia.

The invention will be illustrated by the following non-limiting examples.

EXAMPLE 1

Preparation of 9-(2-{[di(tert-butyl)phosphino]methyl}-2-propenyl)-9-phosphabicyclo[3.3.1]nonane

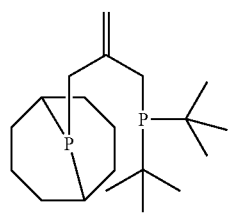

FIG. 1: 9-(2-{[di(tert-butyl)phosphino]methyl}-2-propenyl)-9-phosphabicyclo[3.3.1]nonane A mixture of di-tert-butylphoshine (5 g, 34.1 mmol) and 3-chloro-2-chloromethyl-1-propene (14.04 g, 69 mmol) was dissolved in degassed acetonitrile (70 ml) and heated to 60° C. for 16 hours. The solvent was removed in vacuo and the product was suspended in hexane (50 ml). After filtration the product was washed with hexane (2 times 40 ml). The white solid salt was neutralized in a mixture of toluene (50 ml) and water (30 ml) with HNEt2 (5 ml) under reflux conditions. The toluene layer was separated, washed with water (2 times 30 ml) and removed in vacuo, to yield 3.14 g (40%) of di(tert-butyl)[2-(chloromethyl)-2-propenyl]phosphine. The product could be characterized by showing a distinct resonance signals in $^{31}$P NMR at δ=+21.7 ppm.

2.82 g (20 mmol) of the 9-phosphabicyclo[3.3.1]nonane was dissolved in THF (90 ml). To this solution, a 1.6 M solution of n-BuLi in hexane (12.5 ml, 20 mmol) at −50° C. was added. The mixture was allowed to warm to 0° C. for fifteen minutes and then cooled to −70° C., after which and a solution of 4.7 g (20 mmol) di(tert-butyl)[2-(chloromethyl)-2-propenyl]-phosphine obtained as described above in 10 ml THF was added. The mixture was allowed to warm to ambient temperature, and was subsequently quenched with water (5 ml). The solvents were removed in vacuo and toluene (60 ml) was added. The mixture was washed twice with water (40 ml and 20 ml) and the toluene was removed in vacuo giving 6.71 g of a red/orange oil. The product was crystallized twice from (boiling) methanol, giving a white solid (2.83 g, 42%). The product could be characterized by showing two distinct resonance signals in $^{31}$P NMR at +22.1 ppm and −36.5 ppm.

EXAMPLE 2

Preparation of 8-(2-{[di(tert-butyl)phosphino]methyl}-2-propenyl)-1,3,5,7-tetramethyl-2,4,6-trioxa-8-phosphatricyclo[3.3.1.1.{3,7}]decane

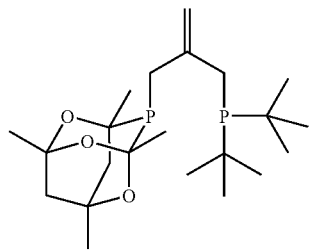

FIG. 2: 8-(2-{[di(tert-butyl)phosphino]methyl}-2-propenyl)-1,3,5,7-tetramethyl-2,4,6-trioxa-8-phosphatricyclo [3.3.1.1.{3,7}]decane To a solution of HPCage*BH3 (1.34 g, 5.83 mmol; Pcage=1,3,5,7-tetramethyl-2,4,6-trioxa-8-phosphatricycle-[3.3.1.1.{3,7}]decane) in THF (20 ml) was added a 1.6 M solution of n-BuLi in hexane (3.64 ml, 5.83 mmol) at −78° C. The mixture was allowed to warm to 0° C. for fifteen minutes and cooled to −78° C. again, after which a solution of di(tert-butyl) [2-(chloromethyl)-2-propenyl]-phosphine as described under (1.37 g, 5.83 mmol) in THF (5 ml) was added. The reaction mixture was allowed to warm to RT. HNEt$_2$ (10 ml) was added and the reaction mixture was refluxed for a few hours, until NMR-measurements showed that the deprotection was complete). Subsequently, the solvents were removed in vacuo, and the solid product was recrystallized from methanol (50 ml) upon gradual cooling. The isolated yield was 1.5 g (62%), and the product could be characterized by showing two distinct resonance signals in $^{31}$P NMR at +20.3 ppm (P-tert,Bu) and −34.3 ppm (P-Cage).

EXAMPLE 3

Preparation of 8-(2-{[di(tert-butyl)phosphino]methyl}phenyl)-1,3,5,7-tetramethyl-2,4,6-trioxa-8-phosphatricyclo[3.3.1.1.{3,7}]decane

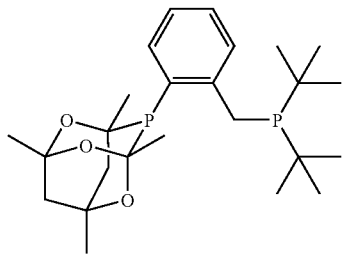

FIG. 3: 8-(2-{[di(tert-butyl)phosphino]methyl}phenyl)-1,3,5,7-tetramethyl-2,4,6-trioxa-8-phosphatricyclo-[3.3.1.1.{3,7}]decane 8.25 g (33 mmol) 2-bromobenzylbromide and 5 g (34.2 mmol) di-tert-butyl phosphine in 40 ml degassed acetonitrile were measured into a 100 ml glass reactor under an inert atmosphere, and then stirred for a period of 12 hours at ambient temperature. The acetonitrile was then removed in vacuo and 30 ml degassed toluene, 30 ml degassed water and 7.5 ml triethylamine were added. To this mixture 10 ml ethanol was added to improve phase separation. Upon phase separation, the upper layer containing the toluene was separated and evaporated to dryness. The remainder was 9 g (28.6 mmol, 87%) of (2-bromobenzyl)(di-tert-butyl)phosphine as a light yellow oil exhibiting a resonance peak in $^{31}$P NMR at +34.16 ppm.

2.5 g (7.9 mmol) of the thus obtained 2-bromobenzyl(di-tert-butyl)phosphine, 2.24 g DABCO (20 mmol), 1.94 g 1,3,5-trimethyl-4,6,9-trioxa-2-phosphatricyclo[3.3.1.1{3,7}]decane (9 mmol) and 0.23 g Pd(PPh$_3$)$_4$ (0.2 mmol) in 10 ml toluene were added into a 250 ml glass vessel under inert atmosphere, and the content of the vessel was heated to 140° C. under stirring for 12 hours. The mixture was than allowed to cool to 100° C., and was then filtered. The filtrate was cooled to room temperature, then 30 ml of methanol added were added and the mixture cooled for a period for 12 hours to −35+ C., 8-(2-{[di(tert-butyl)-phosphino]-methyl}phenyl)-1,3,5,7-tetramethyl-2,4,6-trioxa-8-phosphatricyclo[3.3.1.1{3,7}]decane was isolated as yellow crystals (2.2 g, 4.9 mmol, 62%), and could be characterized by showing two distinct resonance signals in $^{31}$P NMR at +38.08 and −38.96 ppm.

EXAPMLES 4 TO 6 AND COMPARATIVE EXAMPLES A, B AND C

Conversion of 1-octene with methanol

A 250 ml magnetically stirred autoclave, made of HASTELLOY C (HASTELLOY C is a trademark), was successively charged with 40 ml of methanol, 20 ml 1-octene, and 0.5 mmol of methanesulfonic acid, and a catalyst solution comprising 0.1 mmol palladium acetate and 0.2 mmol of the respective ligand in 10 ml of methanol. The autoclave was closed, evacuated, and pressurized with 3 MPa carbon monoxide. The reactor was then heated to 70° C., and maintained at this temperature for 10 hours. Finally the autoclave was cooled, depressurized, and the reaction mixture was analysed with GLC. The turn over frequency is defined as amount of converted products, and given in mol olefin per mol Pd per hour for the batch operation as presented in Table I.

EXAMPLES 7 AND 8

Conversion of ethylene with methanol

A 250 ml magnetically stirred autoclave, made of HASTELLOY C (HASTELLOY C is a trademark), was successively charged with 45 ml of methanol, and 0.5 mmol of methanesulfonic acid. The autoclave was closed, evacuated, and pressurized with 3 MPa carbon monoxide and 20 MPa ethylene. The reactor was then heated to 85° C., and a catalyst solution comprising 0.05 mmol palladium acetate and 0.1 mmol of the respective ligand in 5 ml of methanol was injected into the autoclave, thereby raising the carbon monoxide pressure by an additional 5 bar. The autoclave was maintained at 85° C. for 10 hours. Finally the autoclave was cooled, depressurized, and the reaction mixture was analysed with GLC. The turn over frequency is defined as amount of converted products, and given in mol olefin per mol Pd per hour for the batch operation as presented in Table I.

In Example 4 according to the invention, the ligand was 9-(2-{[di(tert-butyl)phosphino]methyl}-2-propenyl)-9-phosphabicyclo[3.3.1]nonane prepare in Example 1. In Examples 5 and 7 according to the invention, the ligand was 8-(2-{[di(tert-butyl)phosphino]methyl}-2-propenyl)-1,3,5,7-tetramethyl-2,4,6-trioxa-8-phosphatricyclo[3.3.1.1{3,7}]decane prepared in Example 2. In Examples 6 and 8 according to the invention, the ligand was 8-(2-{[di(tert-butyl)-phosphino]methyl}phenyl)-1,3,5,7-tetramethyl-2,4,6-trioxa-8-phosphatricyclo[3.3.1.1{3,7}]decane prepared in Example 3. In Comparative Example A, the ligand was a symmetrical ligand with two 9-phosphabicyclo[3.3.1]nonane rings attached to an isobutene structure (9-[2-(9-phosphabicyclo[3.3.1]non-9-ylmethyl)-2-propenyl]-9-phosphabicyclo[3.3.1]nonane). In Comparative Example B, the ligand was the symmetrical bis-di-tert-butyl phosphino-analogue (di(tert-butyl)(2-{[di(tert-butyl)phosphino]methyl}-2-propenyl)phosphine). In Comparative Example C, the ligand was the symmetrical bis-trioxa-adamantyl-ligand (1,3,5,7-tetramethyl-8-{2-[1,3,5,7-tetramethyl-2,4,6-trioxa-8-phosphatricyclo[3.3.1.1{3,7}]dec-8-yl)methyl]-2-propenyl}-2,4,6-trioxa-8-phosphatricyclo[3.3.1.1{3,7}]decane).

In Comparative Example D, the ligand was the symmetrical bis-trioxadamantyl-ligand ([1,3,5,7-tetramethyl-8-{2-[1,3,5,7-tetramethyl-2,4,6-trioxa-8-phosphatricyclo[3.3.1.1.{3,7}]dec-8-yl)methyl]benzyl}-2,4,6-trioxa-8-phosphatricyclo[3.3.1.1{3,7}]decane). In Comparative Example E, the ligand was the symmetrical 1,2-bis(di-tert-butylphosphinomethyl)benzene ([1,2-phenylenebis(methylene)]bis(di-tert-butylphosphine)).

The results are depicted in Table 1.

TABLE I

| Example | Ligand | Substrate | Turn over Frequency [mol/mol Pd/hr] | Selectivity for linear product, [%] |
| --- | --- | --- | --- | --- |
| Ex. 4 | Ex. 1 | 1-Octene | 1500 | 83 |
| Ex. 5 | Ex. 2 | 1-Octene | 15000 | 87 |
| Ex. 6 | Ex. 3 | 1-Octene | 20,000 | 96 |

TABLE I-continued

| Example | Ligand | Substrate | Turn over Frequency [mol/mol Pd/hr] | Selectivity for linear product, [%] |
|---------|--------|-----------|-------------------------------------|-------------------------------------|
| Comp. A | see above | 1-Octene | 150 | 76 |
| Comp. B | see above | 1-Octene | 250 | 67 |
| Comp. C | see above | 1-Octene | 500 | 83 |
| Comp. D | see above | 1-Octene | 50 | 67 |
| Comp. E | see above | 1-Octene | 100 | 97 |
|  |  |  |  | Chemosel. carbonylation product, [%] |
| Ex. 7 | Ex. 5 | Ethene | 20,000 | 99.9 |
| Ex. 8 | Ex. 6 | Ethene | 60,000 | 99.9 |

From the above data, it is clear that the unsymmetrical ligands clearly outperform the symmetrical ligands in catalyst activity and selectivity for the desired linear products. Moreover, the use of two different kinds of substituents $R^1$, $R^2$, $R^4$ and $R^5$, wherein $R^1$ and $R^2$ have a different electron-donating ability on $P^1$ as compared to $R^4$ and $R^5$ on $P^2$, and wherein all substituents $R^1$, $R^2$, $R^4$ and $R^5$ are bonded to the phosphorus atoms via tertiary carbon atoms results in yet unprecedented catalyst activity and selectivity for the linear carbonylation products.

The invention claimed is:

1. A process for the carbonylation of unsaturated compounds by contacting the unsaturated compound with carbon monoxide in the presence of a catalyst system comprising:
   (a) a source of palladium and/or platinum; and
   (b) an unsymmetrical bidentate diphosphine ligand of formula I, $$R^1R^2{>}P^1{-}R^3{-}P^2{<}R^4R^5 \qquad (I)$$

wherein $P^1$ and $P^2$ represent phosphorus atoms; $R^3$ represents a divalent organic bridging group; and $R^1$, $R^2$, $R^4$ and $R^5$ each individually, or $R^1$ and $R^2$ jointly, and/or $R^4$ and $R^5$ jointly represent organic groups that are covalently linked to the phosphorus; and wherein $R^1$, $R^2$, $R^4$ and $R^5$ are chosen in such way, that the phosphino group $R^1R^2{>}P^1$ differs from the phosphino group $P^2{<}R^4R^5$.

2. The process of claim 1, wherein $R^1$ and $R^2$ have higher electron donor ability on $P^1$ than $R^4$ and $R^5$ on $P^2$.

3. The process of claim 1 wherein $R^1$ and $R^2$ independently represent the same or different optionally substituted organic group and which groups are solely connected to each other via the phosphorus atom $P^1$; and wherein $R^4$ and $R^5$ together represent an organic bivalent group linked to the phosphorus atom $P^2$.

4. The process of claim 1 wherein $R^1$, $R^2$, $R^4$ and $R^5$ each represent an organic radical which is covalently connected to the respective phosphorus atom via a tertiary carbon atom.

5. The process of claim 1 wherein $R^1$ and $R^2$ together, or $R^4$ and $R^5$ together represent a 2-phospha-adamantane structure or a phosphinan-4-one structure.

6. The process of claim 1 wherein $R^3$ represents a group $$-R^a{}_m{-}R^b{-}R^c{}_n{-} \qquad (III),$$

wherein $R^a$ and $R^b$ independently represent the same or different optionally substituted methylene groups;
$R^b$ represents an organic group comprising a bivalent bridging group $C^1$-$C^2$ through which $R^b$ is connected to $R^a$ and $R^c$; m and n independently represent a natural number in the range of from 0 to 4, and wherein the rotation about the bond between the carbon atoms $C^1$ and $C^2$ of the bridging group is restricted at a temperature in the range of from 0° C. to 250° C. and wherein the dihedral angle between the plane occupied by the three atom sequence composed of $C^1$, $C^2$ and the atom directly linked to $C^1$ in the direction of $P^1$, and the plane occupied by the three atom sequence $C^1$, $C^2$ and the atom directly linked to $C^2$ in the direction of $P^2$, is in the range of from 0 to 120°.

7. The process of claim 6 wherein $R^b$ represents an aryl group, and wherein m is 0 or 1, n is 1, and the phosphorus atoms $P^1$ and $P^2$ are connected to R through the respective methylene groups $R^a$ or $R^c$ or directly in adjacent positions on the aryl group.

8. The process of claim 6 wherein $R^1$ and $R^2$ represent tertiary butyl groups, and $R^4$ and $R^5$ together represent a 2-phospha-adamantane structure or a phosphinan-4-one structure.

9. The process of claim 1 wherein ethylene is converted to methyl propionate in presence of methanol.

10. The process of claim 1 wherein pentenoic acid is converted to adipic acid.

11. A catalyst composition comprising:
    (a) a source of palladium, and/or platinum; and
    (b) an unsymmetrical bidentate diphosphine ligand of formula I, $$R^1R^2{>}P^1{-}R^3{-}P^2{<}R^4R^5 \qquad (I)$$

wherein $P^1$ and $P^2$ represent phosphorus atoms; $R^3$ represents a divalent organic bridging group; and $R^1$ and/or $R^2$ are tertiary alkyl groups, and $R^4$ and $R^5$ together represent an optionally substituted divalent cycloaliphatic group, wherein the cycloaliphatic group is linked to the phosphorus atom via two tertiary carbon atoms; and wherein $R^1$, $R^2$, $R^4$ and $R^5$ are chosen in such way, that the phosphino group $R^1R^2{>}P^1$ differs from the phosphino group $P^2{<}R^4R^5$.

12. The catalyst composition of claim 11 wherein $R^1$ and $R^2$ represent tertiary butyl groups, and $R^4$ and $R^5$ together represent a 2-phospha-adamantane structure or a phosphinan-4-one structure.

13. The catalyst composition of claim 11 wherein $R^3$ represents a group wherein $R^a$ and $R^b$ independently represent the same or different optionally substituted methylene groups;
$R^b$ represents an organic group comprising a bivalent bridging group $C^1$-$C^2$ through which $R^b$ is connected to $R^a$ and $R^c$; m and n independently represent a natural number in the range of from 0 to 4, and wherein the rotation about the bond between the carbon atoms $C^1$ and $C^2$ of the bridging group is restricted at a temperature in the range of from 0° C. to 250° C., and wherein the dihedral angle between the plane occupied by the three atom sequence composed of $C^1$, $C^2$ and the atom directly linked to $C^1$ in the direction of $P^1$, and the plane occupied by the three atom sequence $C^1$, $C^2$ and the atom directly linked to $C^2$ in the direction of $P^2$, is in the range of from 0 to 120°.

14. The catalyst composition according to claim 13, wherein $R^b$ represents an aryl group, and wherein m is 0 or 1, n is 1, and the phosphorus atoms $P^1$ and $P^2$ are connected to R through the respective methylene groups $R^a$ or $R^c$ or directly in adjacent positions on the aryl group.

15. The catalyst composition of claim 11 further comprising a source of an anion.

16. An unsymmetrical bidentate diphosphine ligand of formula VI, $$R^1R^2{>}P^1{-}CH^2{-}C(={}X){-}CH^2{-}P^2{<}R^4R^5 \qquad (VI)$$

wherein X represents an oxygen atom, a sulphur atom, an amino group, or a optionally substituted alkylene group; wherein $P^1$ and $P^2$ represent phosphorus atoms; $R^1$, $R^2$, $R^4$ and $R^5$ each individually, or $R^1$ and $R^2$ jointly, and/or $R^4$ and $R^5$ jointly represent organic groups that are covalently linked to the phosphorus; and wherein $R^1$ to $R^4$ are chosen in such way, that the phosphino group $R^1R^2>P^1$ differs from the phosphino group $P^2<R^4R^5$.

17. The unsymmetrical bidentate diphosphine ligand according to claim 16 wherein X represents a methylene group.

18. A catalyst composition comprising an unsymmetrical bidentate diphosphine ligand of claim 16 and a source of palladium, platinum, or rhodium.

19. A catalyst composition comprising an unsymmetrical bidentate diphosphine ligand of claim 17 and a source of palladium, platinum, or rhodium.

20. The catalyst composition of claim 18, further comprising a source of an anion.

* * * * *